United States Patent [19]

List

[11] 4,126,345
[45] Nov. 21, 1978

[54] HANDLING DEVICE FOR SOFT CONTACT LENSES

[76] Inventor: Frederick B. List, 1312 Main St., Lubbock, Tex. 79400

[21] Appl. No.: 864,918

[22] Filed: Dec. 27, 1977

[51] Int. Cl.² .............................................. A61F 9/00
[52] U.S. Cl. .................................................. 294/1 CA
[58] Field of Search ................... 294/1 CA, 64 R, 21; 206/5.1; 351/160; 128/303; 15/104.92

[56] References Cited

U.S. PATENT DOCUMENTS

| | | | |
|---|---|---|---|
| 3,063,083 | 11/1962 | Obitts | 294/1 CA |
| 4,026,591 | 5/1977 | Cleaveland | 294/1 CA |

Primary Examiner—James B. Marbert
Attorney, Agent, or Firm—Fishburn, Gold & Litman

[57] ABSTRACT

A device for handling soft contact lenses comprises a pair of resilient pincer arms, each arm having one end mutually interconnected and a free end spaced apart from the other free end. A lens cup is attached to the interconnected arm ends and is shaped for receiving and holding a sfot contact lens therein. The free end of each pincer arm includes a soft tip connected therewith, which extends outwardly therefrom, is constructed of a resilient, flexible material, and has a terminal surface shaped for frictionally engaging an outer surface of a soft contact lens. The arms are interconnected for positioning the tips on opposing sides of the lens when the soft contact lens is positioned in the eye of a wearer, whereby convergence of the arms folds the lens between the tips for removal of the lens from the eye.

13 Claims, 8 Drawing Figures

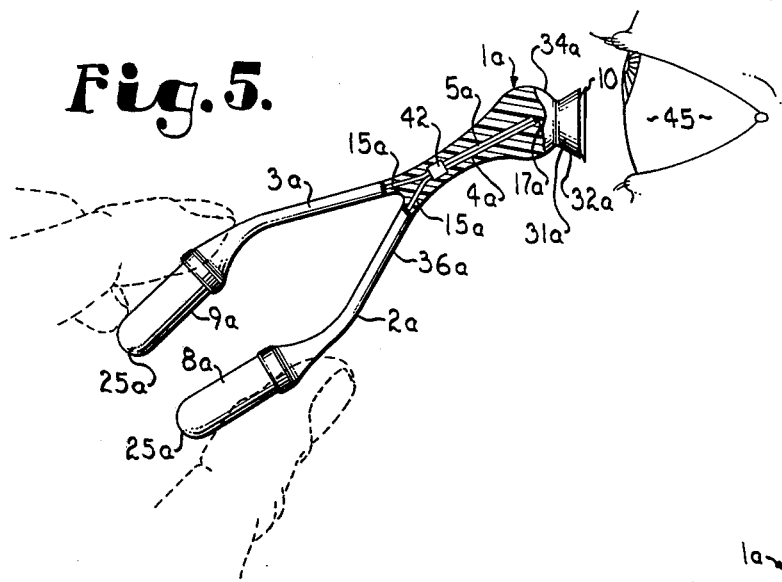
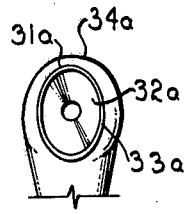
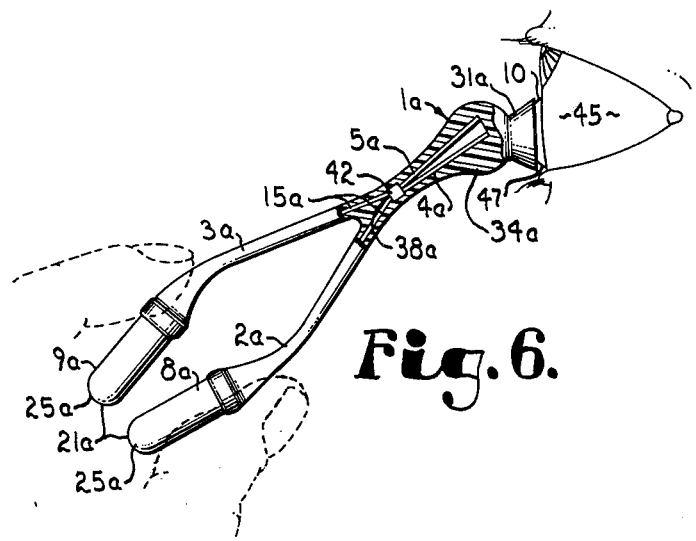
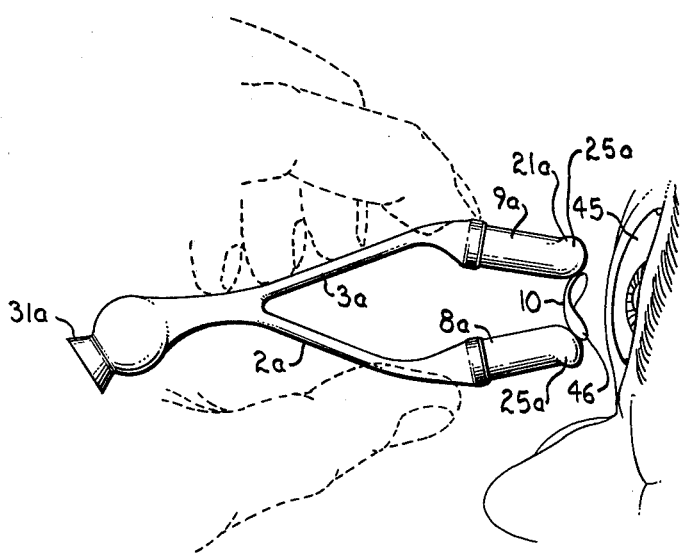

HANDLING DEVICE FOR SOFT CONTACT LENSES

This invention relates to a handling device for contact lenses, and in particular to a device for inserting and removing soft contact lenses.

Various devices have been designed for aiding contact lens wearers in inserting and removing contact lenses from the eye. Structures such as those disclosed in U.S. Pat. Nos. 3,584,908 and 3,934,914 include a suction bulb arrangement for holding the lens in contact with the handler, and are specifically designed to handle "hard" or "contactless" contact lenses, and are not adapted for the use with the recently developed soft contact lenses. A soft contact lens is constructed of a hydrophilic material, which when hydrated, is extremely pliable and requires special asepticizing, cleaning, storage, removal, and insertion techniques. As an example of the unusual characteristics demonstrated by the soft contact lenses, the same must be folded to remove it from the wearer's eye, and must be thoroughly asepticized, preferably by specially designed equipment. Because of the above noted features of the soft contact lenses, handling of the same by the user's fingers often results in injury and/or insult to both the eye and to the lens from fingernails, rough hands, and the like. Also, oil, dirt, and other foreign matter on the user's hands can easily damage the lens and/or cause injury to the eye. The present device is particularly designed for safely handling soft contact lenses.

The principal objects of the present invention are: to provide a device for safely inserting and removing soft contact lenses from a human eye; to provide such a device having pincer arms with soft, pliable tips projecting from each arm free end for removing a soft contact lens from a wearer's eye without causing injury or insult thereto; to provide such a device having a lens cup connected with the other end of the device for inserting the lens into the eye; to provide such a device wherein the cup is disposed at an obtuse, anatomical angle to the pincer arms for easy insertion of the lens into the eye; to provide such a device having an imperforate cover member encasing a major portion of the device for thorough sanitation thereof and clean lens handling; to provide such a device having flexible, tubular tips for non-injurious lens contact and improved user comfort; to provide such a device having a deformable lens cup to facilitate lens insertion; and to provide such a device which is economical to manufacture, efficient use, capable of a long operating life, and particularly well adapted for the proposed use.

Other objects and advantages of this invention will become apparent from the following description taken in connection with the accompanying drawings wherein are set forth, by way of illustration and example, certain embodiments of this invention.

The drawings constitute a part of this specification and include exemplary embodiments of the present invention and illustrate various objects and features thereof.

FIG. 5 is a side elevational view of a second embodiment of the present invention having a deformable lens cup, said device being shown in an open position, and having portions thereof broken away to show internal construction.

FIG. 6 is a side elevational view of the second embodiment of the device, shown in a closed position, and having portions thereof broken away.

FIG. 7 is an elevational view of the device illustrated in FIG. 6, wherein the lens cup portion thereof is deformed to an ovate shape to assist the disengagement of the lens from the cup, the deformation being exaggerated for purposes of illustration.

FIG. 8 is a top plan view of the device illustrated in FIG. 5, shown removing a soft contact lens from a wearer's eye.

Figure 1:
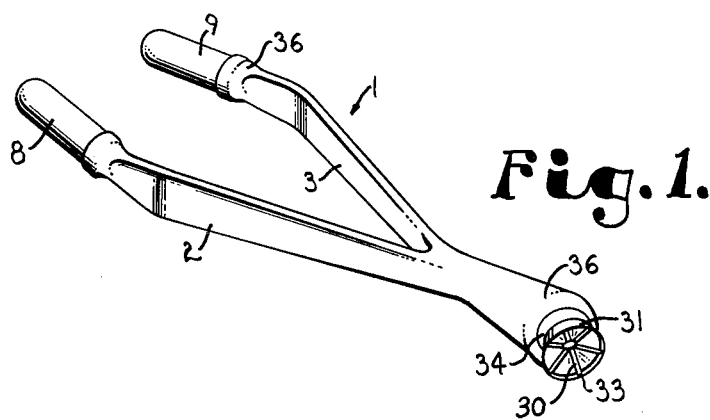
FIG. 1 is a perspective view of a handling device for soft contact lenses embodying the present invention.

Referring more in detail to the drawings:

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a device for handling soft contact lenses embodying the present invention, and comprises a pair of pincer arms 2 and 3, each having one end 4 and 5 respectively, mutually interconnected and a free end 6 and 7 respectively which are mutually spaced apart. The free end of each of the pincer arms 2 and 3 includes a soft tip 8 and 9 respectively which extends outwardly from the free end and is connected therewith. During use, the tips 8 and 9 are positioned on opposing sides of a soft contact lens 10 (FIG. 8), and convergence of the arms 2 and 3 folds the lens 10 between the tips for removal of the same from the wearer's eye.

Figure 2:
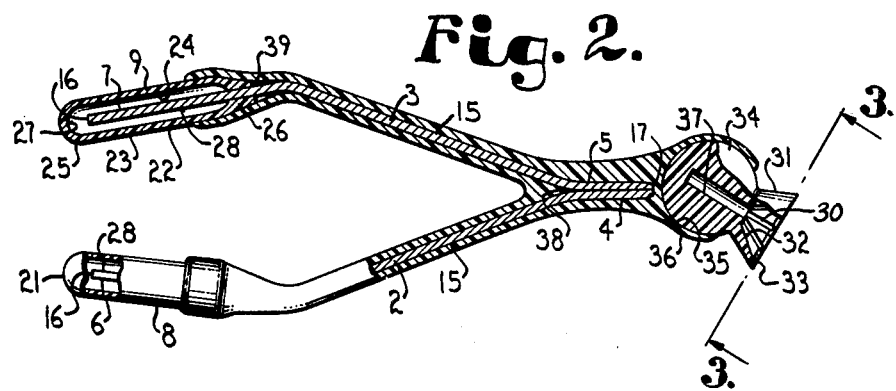
FIG. 2 is a side elevational view of the device having portions thereof broken away to reveal internal construction.

The arms 2 and 3 are interconnected at ends 4 and 5 thereof and are spaced apart at their free end 6 and 7 in the nature of pincers, tweezers, or the like. Resilient means are connected with the arms 2 and 3 and urge the tips 8 and 9 divergingly apart to an open position, as shown in FIGS. 1 and 2. In this example, the arms 2 and 3 are constructed of a rigidly resilient material, such as spring steel or the like, and form a pair of opposing substantially flat leaf springs which resiliently urge the arms toward their open position. The illustrated arms 2 and 3 are similarly shaped, and each has a rectilinear midportion 15 and inwardly bent free ends 6 and 7, with the interconnected ends 4 and 5 being flat and joined along an elongate portion. The terminal edge 16 of each free end 6 and 7 is preferably rounded and free of sharp edges, as is the opposing end edge 17 of the interconnected arms ends. The illustrated free ends 6 and 7 are positioned inwardly at an obtuse angle, in the nature of 150° with respect to the rectilinear midportions 15.

The tips 8 and 9 are connected with and extend outwardly of the arm free ends 6 and 7, and are constructed of a soft, resilient, and flexible material, such as natural or synthetic rubber, polymeric resins, and the like. The terminal surface 21 of each tip is smooth and arcuately shaped for non-injurious contact with the soft contact lens 10. The tips 8 and 9 form a sheath or cover for the arm ends 6 and 7, and in this example have a similar bulbous shape and comprise a tubular member 22 having a flexible side wall 23, a central axial aperture 24 and a flexible, hemispherically shaped end 25 with the terminal surface 21. The inner end 26 of the tubular member 22 is tapered and includes an aperture therethrough which snugly receives the free end of the associated arm therein. The tips 8 and 9 are connected with the arm free end by means such as a frictional fit, bonding, or the like. The free ends 6 and 7 of the illustrated arms 2 and 3 respectively extend axially through the central aperture 24 of the tubular member 22, and the terminal edge 16 of the same is spaced apart from the adjacent interior surface 27 of the tubular member end 25. The sides 28 of the free end of each arm are also spaced apart from the interior surface of the tubular member side wall 23. During use, the tubular member 22 and terminal surface 21 of each of the tips 8 and 9 flex to conform with the exterior surface of the lens 10 to alleviate the hazard of injury to the eye and/or lens during lens handling. In the illustrated structure, the tip is positioned coaxially with the arm free end, whereby the tips are angled slightly inwardly toward each other.

Figure 3:
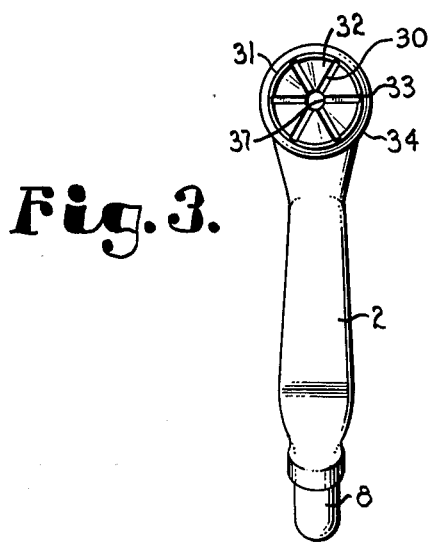
FIG. 3 is an elevational view of the device taken along line 3—3, FIG. 2.

A lens cup 31 is connected with the interconnected arms ends 4 and 5, and is shaped for receiving and holding the soft contact lens 10 therein to facilitate insertion of the lens into the eye. The lens cup 31 has a frustroconically shaped side wall 32 and a tapered end edge 33 which mates with the arcuate shape of the lens 10. The lens cup 31 is also constructed of a soft, flexible and resilient material to prevent damage to the lens 10 and/or the wearer's eye. In this example, the lens cup is positioned at an anatomically selected angle to the arms, to provide a comfortable angle between the wearer's hand and the eye for ease of lens insertion, and may be selectively adjusted to suit the particular user. The illustrated lens cup 31 is disposed at an obtuse angle with respect to the symetrical center line of the arms 2 and 3, in the nature of 120°. The lens cup 31 illustrated in FIGS. 1–3 includes a semispherically shaped base portion 34 pivotally mounted in a mating aperture or socket 35 formed by an outer cover 36, and a central aperture 37 extending from the base of the cup side wall 32 to adjacent the outer portion of the base portion 34. The end edge 17 of the interconnected arm ends 4 and 5 are positioned adjacent to the base portion 34 of the lens cup 31 and support the same. The lens cup side wall 32 is readily flexible to alleviate the hazard of eye injury during lens insertion.

That portion of the lens cup 31 which abuts the soft contact lens 10 may be provided with perforations, raised ribs, or the like, to reduce the capillary action or suction effect created between the two members and to facilitate lens insertion and handling. In the handling device illustrated in FIGS. 1–4, the lens cup 31 is provided with a plurality of radially disposed apertures or slots 30 which are circumferentially spaced in the cup side wall 32 in the shape of flower petals, and extend through the end edge 33.

The cover member 36 is preferably provided, and is shaped to encase the body portion of the lens cup 31 and a portion of each of the arms 2 and 3 to provide a structure which may be thoroughly cleaned and sanitized. The illustrated cover member 36 is imperforate and is constructed of a soft, resilient material. The cover member 36 encases a major portion of the lens cup base 34 thereby forming the socket 35 in which the cup is received and connected for selected pivotal movement therein. The cover member 36 extends from the socket 35, covering the outer surfaces of each of the arms 2 and 3, to a point on the tips 8 and 9 spaced apart from the outer ends 25. The cover member 36 thereby encases the joint area 38 adjacent the interconnected arm ends 4 and 5, as well as joint areas 39 wherein the inner end 26 of the tubular members engage the free end of the arm. The cover member seals tightly against and/or bonds with both the lens cup base 34 and each of the tips 8 and 9 to form a smooth, seam-free imperforate outer surface which may be easily and thoroughly cleaned and sanitized. The cover member 36 is preferably constructed of a liquid, synthetic resin material which may be applied to the arms by means such as dipping, brushing, or the like and then cured to a solidified state.

The reference numeral 1a generally designates another embodiment of the invention (FIGS. 5–8) having means for assisting the expulsion of the lens from the lens cup 31a. Since the lens handler 1a is otherwise substantially the same as the previously described device 1, similar parts appearing in FIGS. 1–4 and 5–8 respectively are represented by the same, corresponding reference numeral except for the suffix "a" in the numerals of the latter. Unlike the rigidly interconnected arm ends 4 and 5 of the first described lens handling device 1, the present embodiment 1a of the present invention has ends 4a and 5a pivotally interconnected at a point spaced apart from the terminal edge 17a of each of the arms, whereby convergence of the tips 8a and 9a causes the ends 4a and 5a to diverge, as illustrated in FIG. 6. The terminal end edges 17a of each of the arms extends into the base 34a of the lens cup 31a to a point disposed adjacent to the frustroconically shaped side walls 32a. The lens cup edge 33a has a generally circular shape for meting with the lens 10 when the arms 2a and 3a are in an open position (FIG. 5). When the arms are manipulated into a converged position (FIG. 6) the arms ends 4a and 5a deform the lens cup body 34a and edge 33a into a generally ovate shape (FIG. 7). In this example, the lens cup 31a is constructed of a flexible and resilient material and is formed integrally with the cover member 36a. The cover member 36a is molded about the arms 2a and 3a in a manner whereby the same urges the arm ends 4a and 5a convergingly together to an abutting position (FIG. 5). The illustrated arms 2a and 3a are pivotally interconnected by a clip member 42 positioned adjacent to the intersection of the mid and end portions 15a and 4a of the arms respectively. The clip 42 allows each of the arm ends 4a and 5a to pivot mutually therein.

Figure 4:
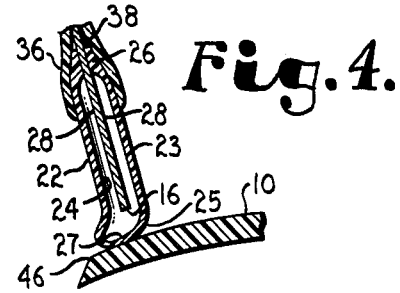
FIG. 4 is an enlarged fragmentary cross-sectional view of a tip portion of the device, shown abutting a portion of a soft contact lens.

In use, both embodiments of the present invention 1 and 1a remove a soft contact lens 10 from an eye 45 in a similar fashion. It is to be noted, that the user of the device may be either the lens wearer himself, or a second person, such as an opthalmologist, or other eye practitioners, nurses or the like, who assist the user in inserting and removing the lenses. As best illustrated in FIG. 8, with the eye of the wearer turned upwardly, and the lower lid of the wearer's eye retracted downwardly, the lens 10 is slidden downwardly onto the white portion of the user's eye. The above step may be accomplished by the user's fingers or by engaging the lens with one of the tips 8 or 9. The handling device is then positioned between the fingers of one of the user's hands for pincing the arms of the device therebetween and is raised by the user to a position disposed adjacent to the eye from which the lens 10 is to be removed, or extracted. With the arms 2 and 3 in their open position (FIGS. 1 and 2) the tips 8 and 9 of the device are positioned on opposing sides 46 of the lens 10 and are gently, abuttingly engaged therewith. Because the tubular members 22 of the device are soft and non-abuttingly cover the arm ends 4 and 5, they readily conform to the shape of the lens 10, as best illustrated in FIG. 4. The terminal surface 21 of each of the tips 8 and 9 frictionally engages the sides 46 of the lens, and convergence of the arms 2 and 3 by the user folds the lens 10 between the tips thereby removing the lens from the eye 45.

The tips 8 and 9 may be similarly employed to handle the soft contact lens 10 once it has been removed from the wearer's eye. Such uses include transporting the lens from the eye to a storage container (not shown) and/or to and from the asepticizing apparatus (not shown).

Insertion of the lens 10 into the wearer's eye with the first described embodiment 1 of the present invention is achieved by placing the lens 10 concentrically in the lens cup 32. The outer surface 47 of the lens is disposed adjacent to the lens cup edge 33 and generally conforms therewith. The user grasps one or both of the arms 2 and 3 adjacent the tip portions 8 and 9 thereof and translates the lens cup convergingly toward the eye in which the lens is to be placed. The lower lid of the eye is then retracted and the cornea thereof is positioned upwardly in the eye socket, whereby the lens is positioned on the white part of the eye, and adheres thereto by capillary action. Slight massage of the closed eyelid helps to center the lens in the eye.

Lens insertion with the embodiment 1a illustrated in FIGS. 5-7 is substantially similar to the previously described insertion steps, except that after the lens 10 has been positioned adjacent the white portion of the eye, the user converges the tips 8a 1 and 9a. This action causes the opposing arm ends 4a and 5a to diverge thereby deforming the lens cup edge 33a to a generally ovate shape as illustrated in FIG. 7. The degree of ovate distortion is exaggerated in FIG. 7 to facilitate the illustration of this feature. The above described distortion of the lens cup edge 33 assists the disengagement of the lens 10 from the lens cup.

It is to be understood that while I have illustrated and described certain forms of my invention, it is not to be limited to the specific forms or arrangement of parts herein described and shown.

What is claimed and desired to secure by Letters Patent is:

1. A device for handling soft contact lenses comprising:
   (a) first and second arms each having first and second ends; the first ends of said arms being spaced apart and free, and the second ends of said arms being interconnected for relative translation of the first ends of said arms; and
   (b) first and second soft tips connected with the first end of said first and second arm respectively and extending outwardly therefrom; said tips each being resilient and flexible, and having a terminal surface for frictionally engaging an outer surface of a soft contact lens inserted in an eye; said arms being interconnected for positioning said tips on opposing sides of said lens, whereby convergence of said arms folds said lens between said tips for removal of the lens from the eye.

2. A device as set forth in claim 1 wherein:
   (a) the terminal surface of each of said tips has an arcuate shape.

3. A device as set forth in claim 1 including:
   (a) resilient means connected with each of said arms and urging said tips divergingly apart to an open position.

4. A device as set forth in claim 1 wherein:
   (a) the second end of said first and second arms are fixedly interconnected; and
   (b) each of said first and second arms are constructed of rigidly resilient material, and urge said tips divergingly apart to an open position.

5. A device as set forth in claim 1 including:
   (a) a lens cup connected with the second end of each of said arms and shaped for receiving and holding said lens therein.

6. A device as set forth in claim 5 wherein:
   (a) said lens cup is positioned at an obtuse, anatomical angle with respect to said arms for insertion of said lens.

7. A device as set forth in claim 5 wherein:
   (a) said lens cup includes a body portion thereof connected with said arms; and including
   (b) an imperforate cover member encasing said body portion and each of said arms.

8. A device as set forth in claim 1 wherein:
   (a) said first and second tips each comprises a tubular member having a flexible side wall, a central aperture, and a hemispherically shaped outer end integral therewith; and
   (b) the first end of each of said arms is positioned in the central aperture of an associated tubular member and is connected with an inner end thereof; said tip terminal surface being smooth and spaced apart from a terminal edge of the associated arm, whereby during lens removal, the tubular member and terminal surface of each tip flexes to conform to the outer surface of the lens and thereby alleviates the hazard of eye injury.

9. A device as set forth in claim 8 wherein:
   (a) said first end of each of said arms includes sides positioned a spaced apart distance from the interior surface of the side wall of said associated tubular member.

10. A device as set forth in claim 8 including:
    (a) a lens cup connected with the second end of each of said arms and shaped for receiving and holding said lens therein; said lens cup having a body portion; and
    (b) an imperforate cover member encasing said first and second arms, said lens cup body portion and each tubular member inner end; said cover having a smooth continuous outer surface for easy cleaning and thorough sanitation.

11. A device as set forth in claim 1 wherein:
    (a) the second end of each of said arms includes a terminal edge; and
    (b) the second ends of said first and second arms are pivotally interconnected at a point thereon spaced apart from each terminal edge, whereby convergence of said tips diverges said terminal edges.

12. A device as set forth in claim 11 including:
    (a) a lens cup connected with the second end of each of said arms and shaped for receiving and holding said lens therein.

13. A device as set forth in claim 12 wherein:

(a) said lens cup is flexible and resilient, and includes a marginal edge for abuttingly supporting said lens; and
(b) said arm second ends are mounted in said lens cup whereby said marginal edge has a substantially circular shape when said tips are in a diverged position, and said marginal edge has an ovate shape when said tips are in a converged position for assisting the disengagement of said lens from said lens cup.

* * * * *